United States Patent [19]

Highsmith

[11] Patent Number: 5,440,760
[45] Date of Patent: Aug. 15, 1995

[54] DISPOSABLE FACE SHIELD

[75] Inventor: Monte Highsmith, North Richland Hills, Tex.

[73] Assignee: Tecnol Medical Products, Inc., Fort Worth, Tex.

[21] Appl. No.: 191,942

[22] Filed: Feb. 4, 1994

[51] Int. Cl.6 .......................... A61F 9/04; A42B 1/06
[52] U.S. Cl. .................................................. 2/9; 2/11; 128/857
[58] Field of Search .................... 2/9, 10, 11, 15, 410, 2/424, 426, 427, 430, 435, 436, 437, 452, 454, 901, 206, 173, 181.2, 181.6, 431, 433; 128/857, 858, 917

[56] References Cited

U.S. PATENT DOCUMENTS

| | | | |
|---|---|---|---|
| D. 312,331 | 11/1990 | Poettgen | D29/8 |
| D. 326,932 | 6/1992 | Millar | D29/9 |
| 797,293 | 8/1905 | Lang et al. | |
| 1,170,052 | 2/1916 | Diener et al. | |
| 1,337,036 | 4/1920 | Bergmann | |
| 1,923,340 | 8/1933 | Steckler | 2/17 |
| 3,395,406 | 8/1968 | Smith | 2/14 |
| 3,686,690 | 8/1972 | Webb | 2/9 |
| 4,435,852 | 3/1984 | Nesler | 2/436 |
| 4,646,367 | 3/1987 | Hassen | 2/411 |
| 4,701,965 | 10/1987 | Landis | 2/428 |
| 4,825,878 | 5/1989 | Kuntz et al. | 128/857 |
| 4,852,185 | 8/1989 | Olson | 2/9 |
| 4,852,189 | 8/1989 | Duggan | 2/452 |
| 4,864,653 | 9/1989 | Landis | 2/9 |
| 4,872,465 | 10/1989 | Kuntz | 128/857 |
| 4,884,296 | 12/1989 | Nix, Jr. | 2/11 |
| 4,910,804 | 3/1990 | Lidgren | 2/209.3 |
| 4,920,576 | 5/1990 | Landis | 2/9 |
| 4,944,312 | 7/1990 | Smith | 128/857 |
| 4,945,574 | 8/1990 | Dagher | 2/9 |
| 5,113,528 | 5/1992 | Burke, Jr. et al. | 2/9 |
| 5,138,714 | 8/1992 | Smith | 2/9 |
| 5,303,423 | 4/1994 | Gazzara et al. | 2/9 |

FOREIGN PATENT DOCUMENTS

| | | | |
|---|---|---|---|
| 655814 | 1/1938 | Germany | 30D/2001 |
| 688227 | 2/1940 | Germany | 30D/2001 |

OTHER PUBLICATIONS

Eyewear, The Surgical Technologist, Nov. 1992, p. 18.
TECNOL, brochure, Hospital Products Division, "Disposable Face Shield".
"Digi" Sportlens System.
Op-d-op, Inc. visor shield, Materials Management, Mar. 1992.
Splash Protection from Eye Communications, Supervisor TM.
"Splash Mask" TM, Incon.
Face Shield Disposable by BFW, SCM Medical, IC Products, and Eye Communications.
Med-Vue Protective Eye Wear.

*Primary Examiner*—Clifford D. Crowder
*Assistant Examiner*—Michael A. Neas
*Attorney, Agent, or Firm*—Baker & Botts

[57] ABSTRACT

The disposable face shield (10) protects the wearer against airborne particles and droplets possibly containing pathogens. The disposable face shield (10) includes a transparent plastic shield (12) and a cord (50) attached to the transparent plastic shield (12) for securing the shield about the wearer's face. A crescent-shaped foam member (20) is affixed to the transparent plastic shield (12) at an upper-central spot. The foam member further defines at least one gap between the foam member and the transparent plastic shield to provide ventilation. When not in use, the disposable face shield has a generally flat profile for ease of storage and packaging.

20 Claims, 1 Drawing Sheet

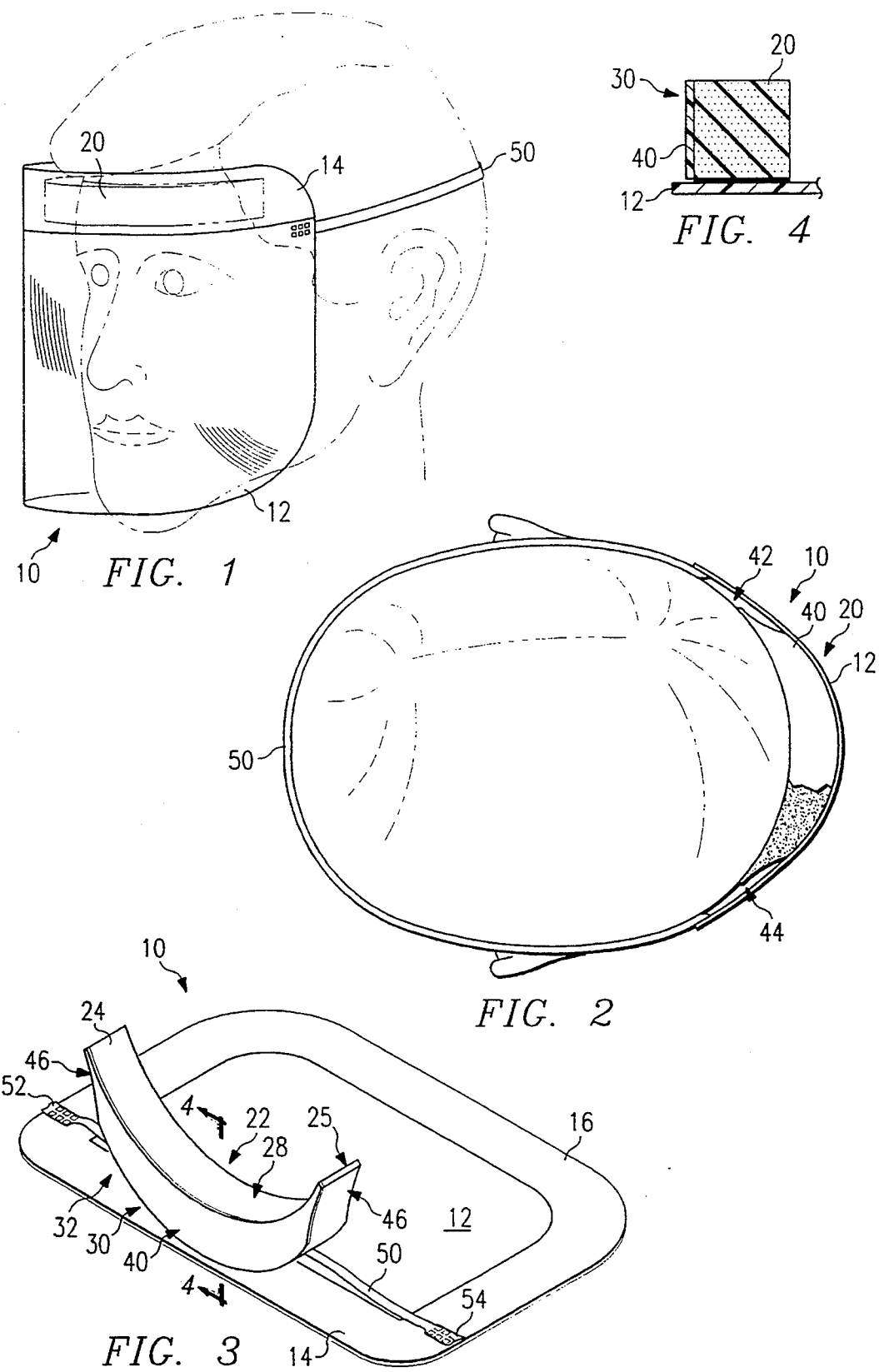

DISPOSABLE FACE SHIELD

TECHNICAL FIELD OF THE INVENTION

This invention relates in general to the field of health care devices and facial protective devices. More particularly, the present invention relates to a disposable face shield.

BACKGROUND OF THE INVENTION

Medical and dental care professionals are exposed to hazardous infectious pathogens on a daily basis. With the spread of acquired immune deficiency syndrome (AIDS) and other deadly and presently incurable diseases, the protection of these professionals from nasal and oral emissions, blood, and other bodily fluids has become more vital than ever. Because the eyes, nose and mouth include regions of thin and penetrable membranes, the face is an area requiring appropriate protection from flying contaminants and particulates.

Several requirements must be met by a facial protection device of this type. It must be light weight and easily worn and removed. It must adequately shield the vital areas of the face yet not obstruct vision. It must provide ample ventilation as not to hamper breathing and to further avoid fogging and accumulation of moisture. In addition, it should be disposable for adequate and safe disposition of contaminants. Because such face protection is disposable and a large number of them may be used, ease of packaging and storage is also an important criteria.

SUMMARY OF THE INVENTION

In accordance with the present invention, a disposable face shield is provided to protect the wearer against air borne particles and droplets possibly containing infectious pathogens.

In one aspect of the present invention, the disposable face shield includes a transparent plastic shield and a stretchable or elastic cord attached to the transparent plastic shield for securing the shield about the wearer's face. A crescent-shaped foam member is affixed to the transparent plastic shield at an upper-central spot. The foam member further defines at least one gap between the foam member and the transparent plastic shield to provide ventilation.

In another aspect of the present invention, the foam member is affixed to the transparent shield at one spot so that the disposable face shield has a generally flat profile for ease of storage and packaging.

In yet another aspect of the present invention, a liquid-impervious film is applied to the foam member to close off its open cell structure.

In another aspect of the present invention, an anti-glare strip is provided along an upper edge or the entire outer edge of the transparent shield to improve the wearer's vision by reducing glare.

In yet another aspect of the invention, a method for fabricating a disposable face shield provides the steps of forming a transparent plastic shield and attaching a cord to the transparent plastic shield for securing the shield about a wearer's face. A foam member is shaped into a generally crescent shape and attached to the transparent plastic shield at an upper-central spot. The foam member is further shaped to define at least one ventilation gap between the foam member and the transparent plastic shield.

Technical advantages of the present invention include the disposable nature of the face shield. Once used where it may have come into contact with harmful pathogens, it may be properly disposed. Furthermore, since it is disposable and a large quantity of them may be used, the ease of packaging and storage provided by its flat profile is tremendously valuable.

Because emergency response vehicles have limited storage space for medical devices and equipment, the flat profile of the disposable face shield allows emergency response personnel to have access to a plentiful supply of the protective face shields.

The anti-glare strip further improves the wearer's vision by reducing the amount of glare striking the wearer's eyes. The attachment of the transparent shield to the foam member at one central location rather than along the entire surface of the foam member reduces the amount of bonding agent required. Additionally, the attachment of the elastic headband to the transparent shield obviates the need to reinforce the somewhat weaker foam member ends. These features contribute to a lowered manufacturing cost of the disposable face shield.

BRIEF DESCRIPTION OF THE DRAWINGS

For a better understanding of the present invention, reference may be made to the accompanying drawings, in which:

FIG. 1 is a perspective view of a disposable face shield according to the teachings of the invention being worn about a person's face;

FIG. 2 is a top view of a disposable face shield in use;

FIG. 3 is a perspective view of a disposable face shield lying flat for ease of packaging and storage; and FIG. 4 is a cross-sectional view of the foam member along line 4—4 in FIG. 3.

DETAILED DESCRIPTION OF THE INVENTION

The preferred embodiment of the present invention and its advantages are best understood by referring to FIGS. 1-4 of the drawings, like numerals being used for like and corresponding parts of the various drawings.

Disposable face shield 10 is shown in FIGS. 1 and 2 as being worn about the face of a person to protect against flying particulates, liquid spray and bodily fluids. Disposable face shield 10 includes a transparent shield 12 of an appropriate size to protect substantially the entire facial region of an average adult. Preferably, the length of transparent shield 12 enables it to extend to or beyond the wearer's chin and the width thereof is sufficient to substantially enclose the wearer's face. Naturally, disposable face shield 10 may include transparent shields 12 of smaller or larger sizes when necessary to serve different purposes. Transparent shield 12 may be constructed of any transparent, liquid-impermeable and light-weight material, such as polyester, polycarbonate, and the like.

Transparent shield 12 may incorporate a non-reflective or darkened strip 14 positioned along an upper edge thereof to reduce the amount of glare reflecting off transparent shield 12 and into the wearer's eyes. Additionally, darkened strip 14 may also reduce the amount of overhead light shinning directly into the wearer's eyes. Darkened strip 14 may be fabricated by printing a dark color onto the desired location of transparent shield 12 by known processes. Darkened strip 14 also may be formed by laminating or otherwise affixing a dark colored strip of vinyl thereon. The resultant darkened strip 14 may be opaque or remain slightly transparent. Alternatively, the non-reflective surface may be formed by mechanical or chemical etching. Referring also to FIG. 3, a non-reflective or darkened strip 16 is further provided along the lower and side outer regions of transparent shield 12 to further improve the wearer's vision by reducing the amount of reflected glare that may strike the wearer's eyes. Darkened strips 14 and 16 may be integrated into one strip.

Transparent shield 12 is attached to a foam member 20 acting as a spacer between transparent shield 12 and the wearer's face. Foam member 20 has a central region 22, two tapering ends 24 and 25, a forehead-engaging surface 28, a top surface 30, and a forward surface 32 facing and contacting transparent shield 12. Central region 22 of foam member 20 has a thickness appropriate for establishing the spacing between transparent shield 12 and the face. Two ends 24 and 25 curve inwardly to form about the wearer's forehead have a tapering thickness. In effect, the spacing between transparent shield 12 and the wearer's face is at a maximum at or near the wearer's nose and mouth, and at a minimum near the sides of the wearer's face.

Foam member 20 is preferably attached to transparent shield 12 at one central spot on forward surface 32, so that when face shield 10 is not in use, transparent shield 12 is able to lie flat, as shown in FIG. 3. Any suitable adhesive, glue, bonding agent or bonding process may be used for securely affixing foam member 20 to transparent shield 12. Since face Shield 10 is disposable, a large quantity may need to be stored and used. The flat profile of disposable face shield 10 therefore facilitates bulk packaging and storage.

In a preferred embodiment, foam member 20 may be fabricated from a number of light-weight and flexible materials including polyester foam, polyurethane foam, latex foam, neoprene sponge, PVC blends, and the like. These materials provide flexibility and some rigidity so that foam member 20 may form closely and comfortably to the contours of the wearer's forehead. In addition, top surface 30 of foam member 20 may include a liquid-impermeable skin or film 40 to close off the open cells in foam member 20. Foam member film 40 may be formed by applying a liquid which dries into a solid film or by affixing a solid film of appropriate size and shape. Alternatively, foam material having a natural film surface 40 may be used to form foam member 20. A liquid-impervious polyurethane or polyethylene, such as one manufactured by Tuftain Corporation, may be used. By closing off the open foam cells at top surface 30 of foam member 20, the likelihood of any flying contaminants and liquids coming into contact with the wearer's face becomes even more remote.

In FIGS. 2 and 3, it may be easily seen that tapered ends 24 and 25 of foam member 20 are specially formed to leave ventilation gaps 42 and 44 between transparent shield 12 and the wearer's forehead or temple region. In particular, tapered ends 24 and 25 are fashioned so that small portions thereof are removed, leaving a discontinuous surface 46 in the curvature of forward surface 32. Since the intended purpose of gaps 42 and 44 is to provide ventilation, the shape thereof may vary. Therefore, gaps 42 and 44 may be triangular, curved, or straight. However, the size of ventilation gaps 42 and 44 is preferably small so that airborne contaminants do not easily gain access to the wearer's face.

Disposable face shield 10 further includes a headband 50 for securely positioning the shield over the wearer's face. Headband 50 is of a construction that adapts to a varying circumferences of heads and provides adjustable tension around the wearer's head, such as tieable cords or an elastic band. Headband 50 has two ends 52 and 54, which are attached to the upper and outer edges of transparent shield 12. Preferably, headband 50 is fabricated from a heat-bondable elastic material, including LYCRA TM, GLOSPAN TM, polyurethane elastomeric tape, or any elastic material surrounded by a heat-bondable cover or carrier made of polyester, polypropylene, nylon, or any combination thereof. When non-heat bondable elastic material is used, such as natural rubber, a heat-bondable carrier should be used if the intended method of affixing headband 50 to transparent shield 12 is by heat bonding. Other known methods of attachment are also contemplated, including ultrasound bonding and like techniques.

Note that since headband 50 is attached to transparent shield 12 rather than foam member 20, affixing foam member 20 to transparent shield 12 at one central location is possible because the tension of headband 50 pulls and forms transparent shield 12 over foam member 20 and the wearer's face. In addition, since headband 50 may experience varying degrees of tension as disposable shield 10 is being put on, worn, and removed, its attachment to transparent shield 12 obviates the need to reinforce weaker tapered ends 24 and 25 of foam member 20 if headband 50 were affixed thereto. Recall that the central spot attachment of foam member 20 to transparent shield 12 also provides the flat profile for ease of packaging and storage and reduced manufacturing cost. The darkened or non-reflective strip along the edge of transparent shield 12 further advantageously blocks glaring light from the wearer's eyes.

Although the present invention and its advantages have been described in detail, it should be understood that various changes, substitutions and alterations can be made therein without departing from the spirit and scope of the invention as defined by the appended claims.

What is claimed is:

1. A disposable face shield comprising:
   a generally flat and flexible transparent plastic shield;
   a cord attached to said transparent plastic shield for securing said shield about a wearer's face; and
   a foam member having a generally crescent shape being coupled to said transparent plastic shield solely at an upper-central spot thereby enabling said transparent plastic shield to lie flat when not worn, said foam member having a contour defining at least one ventilation gap between said foam member and said transparent plastic shield when said face shield is being worn.

2. The disposable face shield, as set forth in claim 1, wherein said transparent plastic shield includes a non-reflective surface along its upper edge.

3. The disposable face shield, as set forth in claim 1, wherein said transparent plastic shield includes a non-reflective surface along its entire outer edges.

4. The disposable face shield, as set forth in claim 1, wherein said foam member has a liquid-impermeable upper surface.

5. The disposable face shield, as set forth in claim 1, further comprising a liquid-impermeable skin formed on an upper surface of said foam member.

6. The disposable face shield, as set forth in claim 1, wherein said cord is elastic.

7. The disposable face shield, as set forth in claim 1, wherein said cord is constructed of a heat-bondable elastic, said cord being heat-bonded to said transparent plastic shield.

8. The disposable face shield, as set forth in claim 1, wherein said foam member has two outer ends each having a contour defining a ventilation gap between said foam member and said transparent plastic shield when the disposable face shield is being worn.

9. The disposable face shield, as set forth in claim 8, wherein said foam member two outer ends are shaped to provide ventilation gaps.

10. The disposable face shield, as set forth in claim 1, wherein said transparent plastic shield includes a darkened anti-glare strip along its upper edge.

11. The disposable face shield, as set forth in claim 1, wherein said transparent plastic shield includes a darkened anti-glare strip along its entire outer edges.

12. A disposable face shield comprising:
a generally flat and flexible transparent plastic shield having a non-reflective surface along its upper edge;
a headband bonded to said transparent plastic shield near said upper edge thereof for securing around a wearer's head;
a foam member having a forehead-engaging surface for substantially and resiliently forming to the wearer's forehead, said foam member being coupled to said transparent plastic shield solely at a central spot near said transparent plastic shield upper edge thereby enabling said transparent plastic shield to lie flat when not worn, said foam member having a thickness creating a predetermined spacing between said transparent plastic shield and the wearer's face, said foam member further having two outer ends each having a contour defining a ventilation gap between said foam member and said transparent plastic shield; and
a liquid-impermeable skin formed on an upper surface of said foam member.

13. The disposable shield, as set forth in claim 12, wherein said non-reflective surface further comprises a darkened anti-glare strip extending along the entire outer edges of said transparent plastic shield.

14. The disposable face shield, as set forth in claim 12, wherein said headband is constructed of a heat-bondable elastic.

15. The disposable face shield, as set forth in claim 12, wherein said transparent plastic shield extends slightly beyond the wearer's face.

16. A method for fabricating a disposable face shield comprising the steps of:
forming a transparent plastic shield;
attaching a cord to said transparent plastic shield for securing said shield about a wearer's face; and
shaping a foam member into a generally crescent shape and coupling said foam member to said transparent plastic shield solely at an upper-central spot, and shaping said foam member to define at least one ventilation gap between said foam member and said transparent plastic shield.

17. The method, as set forth in claim 16, further comprising the step of incorporating a darkened strip along an upper edge of said transparent plastic shield.

18. The method, as set forth in claim 16, further comprising the step of storing the disposable face shield flat.

19. The method, as set forth in claim 16, further comprising the step of applying a liquid-impervious film to said foam member.

20. The method, as set forth in claim 16, wherein said cord attaching step includes the step of bonding an elastic cord to the upper outer edge of said transparent plastic shield.

* * * * *